US006576134B1

(12) United States Patent
Agner (10) Patent No.: US 6,576,134 B1
(45) Date of Patent: Jun. 10, 2003

(54) METHOD FOR DISPLACEMENT CHROMATOGRAPHY (76) Inventor: Erik Agner, Svaneveien 19 B, N-1187 Oslo (NO)

( * ) Notice: Subject to any disclaimer, the term of this patent is extended or adjusted under 35 U.S.C. 154(b) by 0 days.

(21) Appl. No.: 09/807,905
(22) PCT Filed: Oct. 20, 1999
(86) PCT No.: PCT/GB99/03463
§ 371 (c)(1),
(2), (4) Date: Apr. 19, 2001
(87) PCT Pub. No.: WO00/23798
PCT Pub. Date: Apr. 27, 2000

(30) Foreign Application Priority Data

Oct. 20, 1998 (GB) .............................. 9822963

(51) Int. Cl.⁷ .............................................. B01D 15/08
(52) U.S. Cl. ...................... 210/635; 210/656; 210/198.2
(58) Field of Search .................................. 210/635, 656, 210/659, 198.2; 530/413, 417

(56) References Cited

U.S. PATENT DOCUMENTS

| 5,149,436 | A | * | 9/1992 | Taniguchi | 210/656 |
| 5,427,686 | A | * | 6/1995 | Asher | 210/635 |
| 5,439,591 | A | * | 8/1995 | Pliura | 210/635 |
| 5,449,461 | A | * | 9/1995 | Ito | 210/635 |
| 5,545,328 | A | * | 8/1996 | Pliura | 210/635 |
| 5,851,400 | A | * | 12/1998 | Fret | 210/635 |
| 6,239,262 | B1 | * | 5/2001 | Cramer | 210/635 |
| 6,245,238 | B1 | * | 6/2001 | Agner | 210/635 |
| 6,379,554 | B1 | * | 4/2002 | Kearney | 210/659 |

FOREIGN PATENT DOCUMENTS

WO  WO 98/46623  * 10/1998 .............. 210/198.2

OTHER PUBLICATIONS

Hodges, "Multi–Column Preparative Reversed–Phase Sample Displacement of Peptides" Journal of Chromotography vol. 548, No. 1/02 pp. 267–280.*
Veeraragavan, "Sample Displacement Mode Chromatography: Purification of proteins by use of a high performance anion exchange column" Journal of Chromatography, vol. 541 Mar. 1991, pp. 207–220.*

* cited by examiner

Primary Examiner—Ernest G. Therkorn
(74) Attorney, Agent, or Firm—The Firm of Hueschen and Sage (57) ABSTRACT A method of sample displacement chromatography separation which comprises applying a multicomponent sample to one end of a chromatography bed comprising stationary phase material having affinity for components of the sample, causing components of the sample to become distributed along the chromatography bed by passage over the bed of a non-eluting mobile solvent phase, and recovering a desired component of the sample from at lest a portion of the chromatography bed, in which the sample components are applied to the chromatography bed in a non-homogeneous manner such that the concentration of at least one component with relatively low affinity for the stationary phase material is enhanced during an earlier part of sample application and/or the concentration of at least one component with relatively high affinity for the stationary phase material is enhanced during a later part of sample application.

12 Claims, 6 Drawing Sheets

METHOD FOR DISPLACEMENT CHROMATOGRAPHY

REFERENCE TO RELATED APPLICATIONS

This application is a 371 of PCT/GB/99/03463 filed Oct. 20, 1999.

This invention is concerned with chromatographic separation, more particularly with a new and improved method of sample displacement chromatography and applications thereof, as well as with apparatus useful in such methods.

During the last 10–15 years displacement chromatography has been suggested as an alternative to liquid chromatography using elution techniques. In elution chromatography, components of a sample are transported along a chromatography bed comprising stationary phase material, e.g. in a column, by a mobile solvent phase. The various components interact at different levels with the stationary phase material and are therefore separated into bands. Displacement chromatography, on the other hands, utilises as mobile phase a displacer solution which has higher affinity for the stationary phase material than do the sample components. In the case of column chromatography the sample components are thereby displaced and driven down the column ahead of the displacer front, competing for adsorption sites and separating into individual component bands as they proceed.

Whereas elution chromatography normally results in substantial dilution of the sample material, displacement chromatography permits recovery of sample components at significantly higher concentrations and generally makes more efficient use of the stationary phase material. However, displacement chromatography does suffer the disadvantage that, to achieve optimum results, operating conditions such as the composition, concentration and flow rate of the displacer solution must be tailored specifically to individual sample types.

Sample displacement chromatography is a self-displacement technique which was first proposed by Hodges et al. [*J. Chromatogr.* 444 (1988), pp. 349–362] for preparative purification of peptides by reversed phase HPLC, and which does away with the need for an extraneous displacer solution. The peptide components are applied to the column input and themselves compete for binding sites on the stationary phase as they are carried through the column or series of columns by an appropriate solvent. The more strongly binding components bind first and displace less strongly binding components to further along the column(s). The components are therefore separated according to their different degrees of hydrophobicity/hydrophilicity and thus their affinity for the stationary phase material. In a representative example a short pre-column is used to trap impurities which are more hydrophobic than the desired sample component, this latter being retained in and saturating the main column, while the more hydrophilic impurities are further displaced and so are washed out of the main column. It is suggested that the size of the pre-column may be adjusted to match the amount of hydrophobic impurities present in a particular sample, whilst the size of the main column may be adjusted to ensure maximum product retention and outflow of hydrophilic impurities.

Curiously Hodges et al. subsequently use gradient elution to recover the desired product from the main column, so that the advantageous potential of displacement chromatography for yielding relatively high concentration product solutions is lost. This would suggest that the initial component separation was incomplete.

Veeraragavan et al. [*J. Chromatogr.* 541 (1991), pp. 207–220] report application of the Hodges technique to purification of proteins using high performance anion exchange chromatography columns. The apparatus used was a low pressure fast protein liquid chromatographic system and again gradient elution was employed; this was presumably felt to be necessary in light of the observation that peak overlaps were a problem in the primary separation procedure. One and two column systems are specifically described, the former being applicable on what are said to be the rare occasions where the desired product is either the most or least strongly binding component. The possibility of using a multi-column system "in which theoretically every component of the protein sample could be fixed to a column of the proper dimensions" is noted.

Multi-column HPLC systems for sample displacement chromatography have in fact been described by Hodges, inter alia in CA-A-2059114. A representative illustration shows the use of ten reversed phase HPLC columns or column segments connected in series for the purification of peptide samples; after the sample material has been loaded and distributed/separated over the train of columns, individual columns or segments may be eluted separately, without resort to gradient elution, the desired product component being recovered in substantially pure form from at least one such column or segment. Advantages of this process are said to be that (i) it allows ten-fold greater loading than comparable gradient elution separations; (ii) it involves minimal use of costly HPLC solvents; (iii) it requires minimal use of fraction analyses; (iv) it avoids the need to use displacer solutions during the actual separation; and (v) operating costs in terms of solvents, column packings and machine usage are much lower than typical gradient elutions.

The Hodges multi-column procedure does not appear to have been widely adopted and has been found in practice to give products with insufficient purity as a result of inadequate resolution of the product from closely related impurities. Moreover, by virtue of the need to operate HPLC procedures at high pressure, typically 80–200 bar, the apparatus required is necessarily complicated and expensive.

WO98/46623, the contents of which are incorporated herein by reference, describes sample displacement chromatography procedures which typically utilise low operating pressures and recover the desired product in a non-gradient manner. Such use of low operating pressures greatly simplifies apparatus requirements, permitting the use of simpler and less expensive pumps, taps, connectors and the like than are required for HPLC systems; the consequential low mobile phase flow rates also give rise to good separation of the sample components. By avoiding use of gradient elution the separation procedure also reduces solvent requirements and may facilitate recovery of the desired product in an advantageously high concentration.

In existing sample displacement chromatography separations, the sample components are introduced in the form of a homogeneous sample solution, so that the individual components are each delivered at a constant concentration throughout the sample application step. The driving force for separation is that weak binders are displaced from the limited number of binding sites on the stationary phase material by the more strongly binding bulk of the product. This proceeds in a continuous manner until the product and other stronger binders are fully retarded in the earlier part of the chromatography bed, thus permitting the more weakly binding impurities to stay bound to the stationary phase material further along the chromatography bed. Once all sample molecules are bound to the stationary phase, no further movement of these molecules will be observed.

A problem which may occur because of such use of homogeneous sample solutions, however, is that molecules of strongly binding components introduced during an early part of sample application may inadvertently be displaced by weaker binders introduced during a later stage of sample application. Since it is not possible for sample molecules to move against the carrier flow, such displaced strong binders may end up as impurities in the desired product part of the chromatography bed. Moreover, a weakly binding component entering the chromatography bed at a late stage of application may compete for a site at an early position of the bed; with only a small fraction of the total sample remaining, the likelihood of displacement from such an early position on the bed is decreased. Therefore this impurity may remain in an unexpectedly early position after the separation and so may contaminate the desired product. In a difficult separation, where several components have a close resemblance to the desired product, this effect may be substantial.

The present invention is based on the finding that loss of resolution in sample displacement chromatography separations resulting from this hitherto unrecognised problem may be significantly reduced if the sample components are applied to the chromatography bed in non-homogeneous form. In this way, a greater concentration of more weakly binding impurities may be introduced in the early part of sample application, with the early introduction of more strongly binding impurities being reduced; unwanted competition involving such impurities may therefore be substantially reduced, with a consequent improvement in product resolution.

Thus, according to one aspect of the present invention there is provided a method of sample displacement chromatography separation which comprises applying a multicomponent sample to one end of a chromatography bed comprising stationary phase material having affinity for components of the sample, causing components of the sample to become distributed along the chromatography bed by passage over the bed of a non-eluting mobile solvent phase, and recovering a desired component of the sample from at least a portion of the chromatography bed, characterised in that sample components are applied to the chromatography bed in a non-homogeneous manner such that the concentration of at least one component with relatively low affinity for the stationary phase material is enhanced during an earlier part of sample application and/or the concentration of at least one component with relatively high affinity for the stationary phase material is enhanced during a later part of sample application.

The desired non-homogeneous application of sample components may be achieved in a variety of ways, for example as described hereinafter; other methods may be devised by those skilled in the art armed with the disclosure of the present specification. In many instances non-homogeneity will be achieved using a preliminary chromatographic separation, either using sample displacement or elution chromatography. It should be emphasised that, whereas multiple chromatographic separations are well known in the art, existing procedures involve successive purifications of a partially purified fraction from a previous separation. This is entirely different from the procedure of the present invention, in which either the whole of a multicomponent sample or a substantial number of the components thereof is subjected to sample displacement chromatography in conjunction with some form of processing which induces an appropriate inhomogeneity in sample composition.

In existing chromatographic purifications involving either elution mode or sample displacement chromatography, it is common to discard fractions containing semi-pure product because of the presence of contaminating impurities which are difficult to remove at a later stage. In the process of the invention, on the other hand, such product-containing fractions from a first separation step may be utilised in subsequent sample displacement chromatography, since the impurity is present only in some of the fractions. It may therefore more efficiently be displaced if present in early-applied fractions or retained if present in late-applied fractions. It will be appreciated that such use of semi-pure product fractions may increase the overall yield as well as strengthening displacement effects.

The desired inhomogeneity in separation processes according to the invention may, for example, be achieved by using a solid sample and a carrier solvent which dissolves the sample components at different rates and thereby applies a concentration gradient to the chromatography bed. Since the solubility of sample components in the carrier solvents used in both normal and reversed phase chromatography will tend to decrease as the binding affinity of the components for the stationary phase material increases, the resulting solubility-induced concentration gradient will enhance the efficiency of the sample displacement separation in accordance with the invention.

Alternatively, where the sample components are already bound to a stationary phase as a result of a previous separation, the extraction conditions may be selected so that the principal component is extracted relatively late and therefore applied relatively late to the sample displacement chromatography bed. In this way the earlier extracted components are more efficiently displaced by this later-applied principal component.

In a further embodiment, a sample may be at least partially separated using a divisible sample displacement chromatography column system, for example as described in the aforementioned WO98/46623, with a number of successive fractions being collected by extraction from successive portions of stationary phase material. Representative systems which may be used here include reversed phase chromatography, extracting with an organic solvent system such as aqueous acetonitrile or acetic acid; ion exchange chromatography, extracting with a salt solution; or hydrophobic interaction chromatography, extracting by a decrease in salt concentration. Following any necessary removal of extracting materials, for example by removal of organic solvents or volatile salts or by operation of a desalting step, the fractions are then applied to the same or a similar chromatography system in order of increased binding affinity, i.e. with any eluted fractions and fractions from the outlet end of the initially used chromatography bed being applied first, and fractions from the inlet end of the initially used chromatography bed being applied last. Such delayed introduction of stronger displacers markedly enhances the efficiency of the second separation.

A still further embodiment may be used to counter the problem that slightly weaker binding impurities are often difficult to remove from the desired product because of tailing effects; this is particularly so when such an impurity constitutes a relatively large fraction of the sample, and arises because a significant amount of this impurity is applied to the chromatography bed at a late stage of the separation process. In such situations where a succession of separations is performed, the desired inhomogeneity may be achieved by applying one or more fractions from a previous separation or separations after application of the current sample to the chromatography bed. If the subsequently applied fraction or fractions are relatively enriched in the desired product, and possibly also in more strongly binding impurities, this will provide an additional separation force on the tailing impurity, resulting in an increased purity for the desired product. It will be appreciated that where a subsequently added fraction is itself in need of further purification, this will occur simultaneously with the above-described displacement of tailing impurity, thereby effectively increasing product throughput.

In a yet still further embodiment, the desired inhomogeneity may be generated by means of an elution mode separation. Thus, for example, gel permeation chromatography may be used to effect a first, partial separation; the eluate may then be applied either directly or in reverse order to the sample displacement chromatography bed, as appropriate. Alternatively, a not-fully resolving reversed phase chromatography separation using isocratic elution may be followed by sample displacement ion exchange chromatography; the proportion of organic solvent used in the first separation may advantageously be selected so that the desired product is principally eluted in a relatively early and concentrated fraction and is to some extent separated from impurities, e.g. with more hydrophobic impurities being retained on the reversed phase chromatography bed. If desired, the initial separation may also be used to remove certain unwanted sample components; thus, for example, salt impurities or partially protected synthetic products may be separated and discarded following reversed phase chromatography, in the latter case because protecting groups contribute to the hydrophobicity of a product. Fractions containing the desired product may then be subjected to sample displacement chromatography, e.g. using an ion exchange stationary phase material.

Representative areas in which separation procedures in accordance with the invention may be used include the following:

In many situations in modern drug design, enormous numbers of compounds are synthesised, often without the time or resources for proper purification or characterisation. A reliable and preferably automated purification system based on sample displacement chromatography may be used to handle several crude products individually and simultaneously, often with the benefit of avoiding other isolation steps.

If a crude peptide derived from solid phase synthesis is purified by cation exchange or reversed phase chromatography, an increased purity will be obtained. To ensure a consistently high purity product, the two steps may be combined in accordance with the process of the present invention. The content of failure sequences in the product may be reduced by the application of a mixture of target peptide having a free amino function in the N-terminal and shorter failure sequences that have been end capped by acetylation, a common procedure in peptide synthesis, in a system intended for sample displacement chromatography. The correct sequence will contain an extra positive charge at pH 2–3, when applied to a cation exchange chromatography bed with aqueous acetic acid as carrier. The capacity of the bed will govern the optimum loading of sample so that most of the product will remain bound to the bed and lower charged impurities will be displaced from the bed.

This first ion exchange chromatography purification may be followed by a reversed phase chromatography purification. The addition of salt to the carrier will extract the peptides from the ion exchange chromatography bed in order of increasing charge. Thus the remaining impurities will be transported onto the reversed phase chromatography bed ahead of the desired product, which will enter the bed relatively late, and so will displace the usually less hydrophobic impurities even more efficiently than when the sample is applied homogeneously.

The product from such a separation may be collected by extraction from the reversed phase chromatography bed, whereafter a high throughput, high resolution analytical system such as HPLC or capillary electrophoresis may be used to perform a purity check to enable combining of sufficiently pure product fractions.

Existing separation/purification procedures are frequently limited by insufficient selectivity which results in cumbersome elution mode separations having to be employed. Typical examples are when there is a small difference in apparent size in gel permeation chromatography or there are small differences in charge or hydrophobicity in isocratically eluted ion exchange and reversed phase chromatography systems respectively. Sample displacement chromatography may also be inefficient where the concentration, and thus the displacing effect, of the desired product in a given sample is low.

An example of this last situation is afforded by Veeraragavan (op. cit.), who endeavoured to purify soybean trypsin inhibitor by means of sample displacement anion exchange chromatography. From the published results, it is clear that the selectivity of the components was inadequate for an efficient sample displacement chromatography separation, so that elution mode gradient separation was employed as the main force for separation. Even so, the chemical purity of the product was not especially high, and recovery was insufficient for an efficient purification.

It can be seen from Veeraragavan's gel electrophoresis results that the most strongly binding, i.e. late eluting, components (product peak 6 and impurity peak 8) appeared to have the lowest molecular weights and therefore the smallest sizes. An improved overall separation may therefore be achieved by running an initial gel permeation chromatography separation and feeding the eluate directly onto an anion exchange chromatography bed. The resulting late application of the "size-sorted" strongly binding components in the second separation step will significantly enhance the efficiency of this sample displacement chromatography step.

Gel permeation chromatography may be used in conjunction with a subsequent sample displacement step in the purification of a wide range of synthetic oligomers and polymers, where the principal impurities will differ in size from the desired product due to an insufficiency or excess of monomer residues, and will also differ in their binding affinities for site specific stationary phase material, for example as a result of differences in hydrophilicity/hydrophobicity, overall charge, charge density etc. It will be appreciated that the application order of eluted components from the gel permeation chromatography should be reversed in the event that late-eluting (i.e. smaller) component fractions from the gel permeation chromatography separation exhibit lower binding affinity for the stationary phase material in the sample displacement chromatography separation than do early eluting (i.e. larger) component fractions.

The above principle may be used in the purification of crude oligonucleotides, where full length sequences have a higher charge than shorter sequences and thereby bind more strongly in anion exchange chromatography, but where sample displacement chromatography alone may give insufficient resolution between a desired product and failure sequences such as an "n−1" impurity. Similarly, in the purification of crude peptide samples by reversed phase sample displacement chromatography, initial gel permeation chromatography and flow reversal of the eluate therefrom may result in smaller less hydrophobic deletion sequences entering the reversed phase chromatography system somewhat ahead of the desired product; such impurities will therefore be much more efficiently displaced during sample displacement chromatography by the increased proportion of product in subsequently applied fractions. It will be appreciated that in such procedures the solvent used in the gel permeation chromatography step should be chosen so that it functions as the carrier in the subsequent sample displacement chromatography separation.

In an alternative procedure for the purification of synthetic oligonucleotides, reversed phase chromatography is used to induce the desired inhomogeneity. The retention time of the sample components on the reversed phase chromatography bed may be adjusted by addition of organic solvent or an ion pairing agent such as triethylamine buffer. Once the desired product begins to elute at basic pH, the eluate flow may be applied directly onto an anion exchange chromatography bed equilibrated with a suitable carrier. Following this sample displacement separation, the product may be extracted by addition of a salt solution and then passed through a desalting column. The desalting step, which in general will be based on gel filtration, may be designed to remove both low molecular weight salt and carrier solution from the previous separation, so as to give a simple aqueous solution of the desired product.

The purification of homopolymers may also be effected utilising the method of the present invention. Representative homopolymers include methoxy-polyethylene glycol (methoxy-PEG) compounds, whose size distribution may be modified by gel permeation chromatography combined with a reversed phase chromatography sample displacement separation. Such a procedure based on separation by size followed by size/hydrophobicity selection narrows the molecular weight range of the product. At the same time, bifunctional impurities which may cause cross-reactions in subsequent applications such as protein modification may also be removed.

Alternatively, PEG compounds may be purified by successive reversed phase chromatography sample displacement separations. A single reversed phase chromatography sample displacement step separates the components to a certain extent, but the selectivity may be insufficient to obtain a single oligomer in high purity. Using the procedure of the present invention, however, a sample may be separated into virtually monodisperse fractions. Thus, after a first separation, fractions of the original sample with narrowed size distribution may be collected from the various parts of the chromatography bed. Once reapplied in the order of migration (smallest molecule-containing fractions first), the displacement effect becomes more pronounced, with less risk of unwanted competition. Improved product purity is thereby obtained for each successive separation in a repetitive process. The whole sample may be reapplied, or parts of it may be removed, e.g. where a fraction contains a large portion of unwanted material or impurities. To increase efficiency, material from other fractionations may also be added, e.g. as hereinbefore described.

Such methods may be applied in industrial-scale processes to permit the economical preparation of highly pure polymer. It will be appreciated that both sample and solvents may be recovered after each separation cycle, thereby reducing operating costs.

In small scale gel permeation chromatography applications, any necessary flow reversal before a second separation step may simply be accomplished using a collection loop consisting of appropriate tubing and switching valves. After collection of eluate in the loop, a valve is switched and the collected sample is directed onto the second chromatography bed in reversed order. The actual volume to be reprocessed may be optimised in advance or may be determined by use of a detection system after the first chromatography bed. If larger volumes are to be processed, appropriate collection devices include fraction collection flasks connected with valves so that reapplication may be performed in reverse order of collection.

Large scale processes may advantageously be performed using a plurality of relatively short columns rather than one or a few longer columns. Thus, for example, it may be convenient to use a series of rectangular shaped columns having a 1×2 m surface area and a bed height of 5–15 cm. Several such columns, for example 10 columns of 10 cm bed height, may be stacked on top of each other and connected with valves so as to be operable in series during sample application or individually during product extraction.

To ensure an even solvent distribution in columns with such a large cross-sectional area, it is desirable to position the inlet at one side on the top of the column and the outlet on the reverse side at the bottom of the column, the inlet and outlet each connecting with arrays of channels which facilitate even distribution of sample solution over the surfaces of the chromatography bed. All sample components will then be transported at an equal rate anywhere over the surface of the stationary phase material, and will pass through the bed by the shortest perpendicular route. Such large chromatography beds may be packed from above, and preferably incorporate spacer bars placed between opposite column walls and having the same height as the column bed height; these bars prevent the stationary phase material from moving sideways in the column and at the same time stabilise the top and bottom frits. Alternatively, for smaller scale separations and/or where stability of the chromatography bed is less critical, chromatography columns with side packing ports, e.g. as described in U.S. Pat. No. 5,667,676, may be employed.

A variety of devices may be constructed to facilitate interfacing with a following step. Thus, for example, a chromatography column device consisting of several columns drilled in a cylinder may be operated either in series or in parallel by rotation of top and bottom sealing plates having appropriate channels such that a sample solution may be passed from an inlet to the top of the first column, from the bottom of that column through a narrow bore tubing to the top of the following column, and similarly through all the columns. During sample extraction and column re-equilibration, the plates are rotated to align a common inlet and individual outlets with each column.

Products obtained from such a column arrangement may be collected in a device which facilitates their further processing. Such a device may be placed below the columns during fraction collection, with one position for each column. After fractions have been extracted and analysed, they may be processed further, for example by direct application to a new column in a suitable sequence. Alternatively, fractions may be concentrated on, for example, a Speedi-vac concentrator, or may be lyophilised in order to remove unwanted solvents.

To simplify material handling, the collecting device may include a hole in the bottom of each compartment to allow the sequential withdrawal of each sample fraction. The holes may be closed by a plate which prevents the fractions from leaking during previous handling; this plate may be rotatable so that one compartment at a time may be connected to a bottom outlet, e.g. fitted with appropriate connecting tubing. The application of pressure to the top of the device will assist in generating a flow of sample fraction from the connected compartment to, for example, a further chromatography bed. Such systems may be automated using simple valve switching, and may incorporate sensors which detect air-liquid interfaces and cause the plate to be turned one step to the next compartment once such an interface is detected.

Column devices may also be based on the 96-well microtiter plate format, the large number of fractions obtainable with this format being advantageous in applications of the process of the invention. If the system is automated, product fractions may be automatically re-injected in an appropriate sequence by a robotic system. The device may be constructed either as described in WO98/46623, or in a form in which a body of columns may be transported between different stations at which equilibration, separation or extraction may be performed by contacting different plates with the top and bottom of the body.

The column and collecting devices described above, with the exception of those described in WO98/46623 and U.S. Pat. No. 5,667,676, constitute a further feature of the present invention.

In general, a variety of stationary phase materials may be employed in the sample displacement chromatography step of separation procedures according to the invention. The requirement that the material has affinity for components of the sample is to be interpreted as requiring that the material has specific sites which are capable of reversible interaction with components of the sample. Gel filtration media, in which samples interact with networks rather than actual sites, are therefore inappropriate, but systems which may be used include straight and reversed phase chromatography, ion exchange chromatography, hydrophobic interaction chromatography and affinity chromatography.

Stationary phase materials used in separation processes according to the invention may be in any convenient form, for example as membranes, gels or microspheres, especially monodisperse microspheres, and will usually be packed into one or more columns, e.g. as hereinbefore described.

The requirement that the mobile solvent phase used in sample displacement separation processes in accordance with the invention is non-eluting is to be interpreted as indicating that the solvent is capable of transporting less-retarded sample components to the next available binding sites but has little or no ability to interfere with interactions between the dissolved sample components and the stationary phase material. A wide range of solvent systems may be used subject to this requirement. Aqueous systems useful in, for example, reversed phase and ion exchange chromatography include water, buffer solutions, solution of bases such as sodium hydroxide, ammonium bicarbonate or ammonium hydroxide, and solutions of acids such as acetic acid or trifluoroacetic acid.

It may be convenient to operate sample displacement separation steps in accordance with the invention at low pressure, for example as described in WO98/46623. Thus the mobile solvent phase may advantageously be applied at a pressure not exceeding 30 bar, e.g. less than 15 bar, preferably less than 10 bar. Operating pressures of around 3 bar may advantageously be employed for commercial separations; overpressures as low as 0.5 bar have been found to give good separations. It may be appropriate to use even lower or no overpressure, depending on the nature of the chromatography bed. Thus, for example, where the bed comprises relatively coarse material, e.g. a coarse polymer gel, the mobile solvent phase may be capable of movement as a result of gravity and/or interaction with the bed material; in such embodiments it may be appropriate to apply a very low overpressure such as 0.1 bar to control rather than to drive the flow of mobile solvent phase.

The pressure source which drives the mobile solvent phase may advantageously be a pressurised gas such as nitrogen, thereby avoiding the need for mechanical pumps and consequently reducing the operating costs of the process.

Recovery of the desired product following sample displacement separation may be achieved by any appropriate method, for example by extraction into an aqueous solvent system or a non-aqueous solvent system (e.g. an organic solvent or supercritical carbon dioxide), by use of a displacer solution having higher affinity for the stationary phase material than does the sample (e.g. aqueous acetonitrile or acetic acid in the case of reversed phase chromatography or a salt solution in the case of ion exchange chromatography), by a decrease in salt concentration (e.g. in the case of hydrophobic interaction chromatography), or by pH change. The use of steady state (i.e. non-gradient) conditions is preferred since it inherently permits the product to be obtained in more concentrated form than is possible using gradient elution. Moreover, since the recovery procedure is totally independent from the separation procedure, the conditions for recovery may be optimised to ensure maximum efficiency of product release and maximum efficiency of use of solvents, displacer solutions etc. without in any way compromising the efficiency of the separation. It is accordingly possible to recover products in concentrations 10- to 100-fold higher than those which may be obtained with gradient or isocratic elution.

The ability to extract products into solvents of choice is also advantageous in allowing recovery of products in stabilised form or in an optimum form for use in subsequent processing steps. Thus, for example, a protein may be extracted using buffer solution at a pH appropriate to maximise stability of the protein.

The following non-limitative examples serve to illustrate the invention. Unless otherwise stated, the columns used were empty separation cartridges which had been filled with SP Sepharose FF (cation exchange) or Lichrosphere C-18 25–40 $\mu$ (reversed phase chromatography). When multiple columns were used, they were connected by a standard adapter (Supelco 5-7020).

EXAMPLE 1

Increasing the Homogeneity of Methoxy-PEG 1000

A commercial methoxy-PEC product was found by mass spectrometry (Maldi-MS, Finnegan Lasermat 2000) to consist of a mixture of oligomers mainly ranging from 9–27 ethylene oxide units. The major component was found to have a MW of 760 Dalton, which was expected to correlate to the sodium adduct of the 16-mer.

a) Separation by Single Reversed Phase Sample Displacement Chromatography Step [Comparative]

Six columns were each packed with 1 ml Lichrosphere 25–40 μm RPC C18 particles, washed with methanol, equilibrated with water and connected in series. A sample of 400 mg methoxy-PEG in 4 ml water was allowed to separate on the columns, whereafter the columns were disconnected and polymer was extracted with methanol from the individual columns. After removal of the solvent and redissolution in water, the fractions were again analysed by Maldi-MS. The composition of the fractions showed that the reversed phase chromatography separation had discriminated on the basis of the size of the polymers, with the smaller and less hydrophobic components being displaced either to a column late in the system or out of the columns.

b) Separation by Succession of Reversed Phase Sample Displacement Chromatography Steps The samples from (a) above between them contained essentially all the components of the original sample, but were to some degree organised on the basis of hydrophobicity and thus size. They were reapplied to the same column system, but this time the earlier fractions enriched in smaller polymers were allowed to enter the system first, followed by the later fractions predominantly containing larger polymers. After repetition of the above-described extraction procedure the individual fractions were found to exhibit significantly improved homogeneity.

Figure 1:
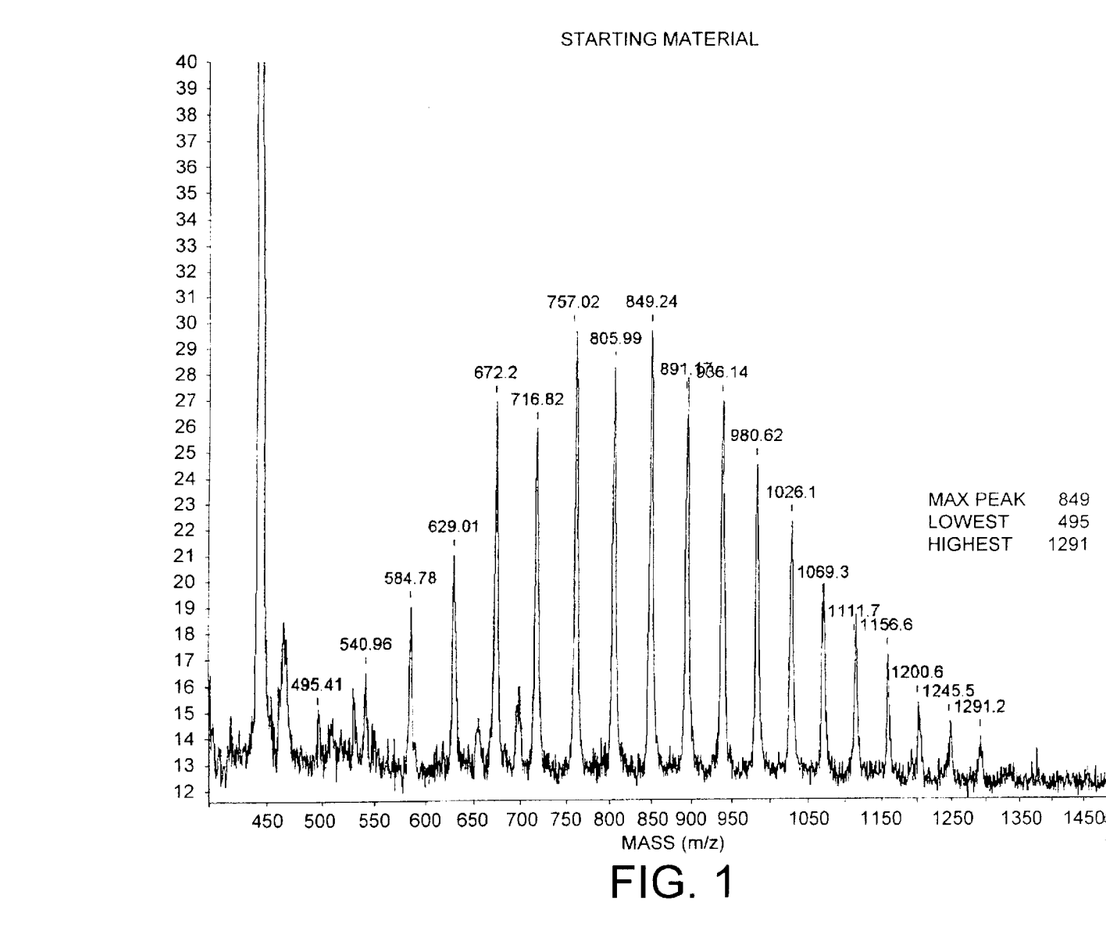
FIG. 1 represents a mass spectrometric analysis of successive methoxy-PEG fractions obtained from the same column position in accordance with the procedure of Example 1.
Figure 2:
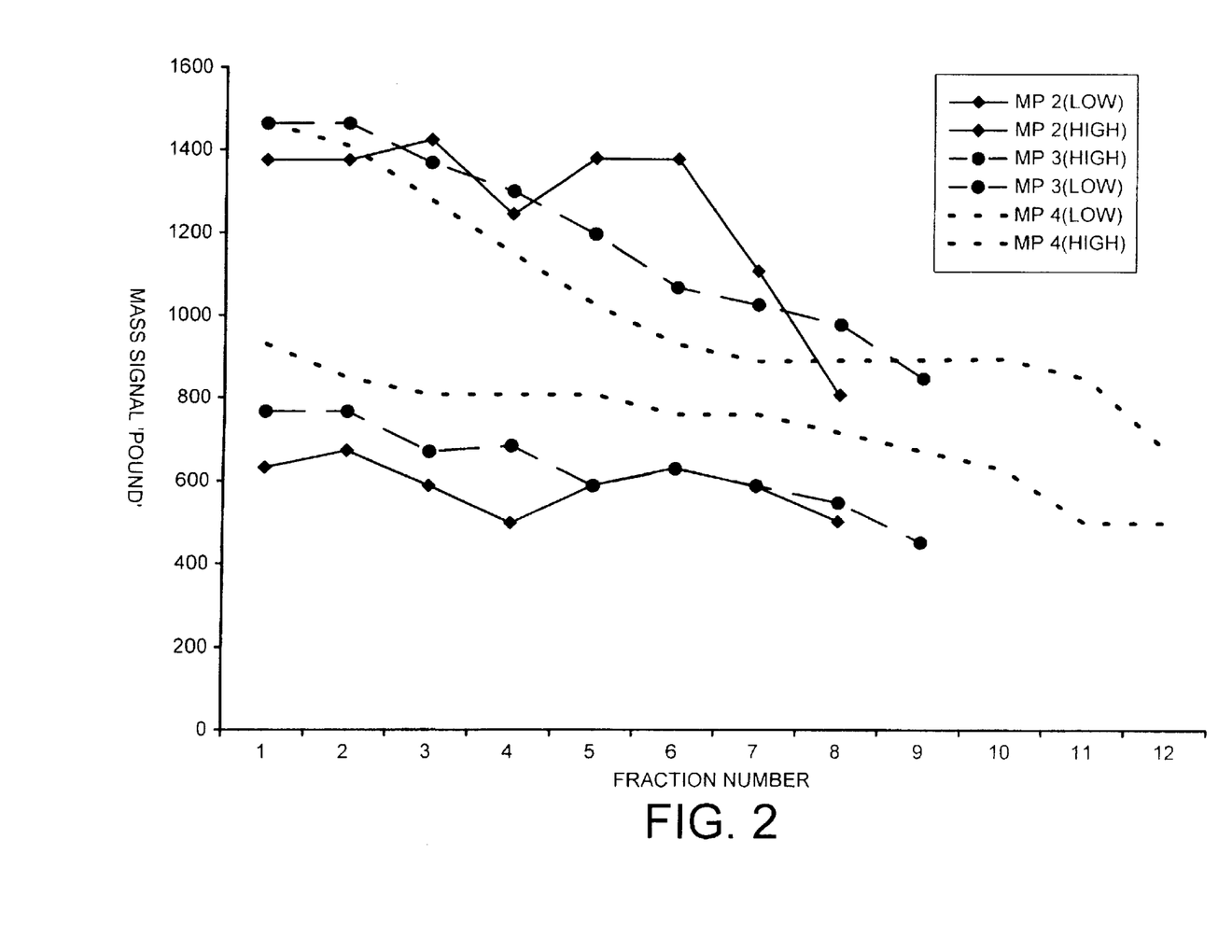
FIG. 2 shows the high and low limits of mass signals observed for methoxy-PEG fractions obtained in accordance with the procedure of Example 1.

The same procedure was repeated a third time to provide fractions with still further enhanced homogeneity. FIG. 1 shows the Maldi-MS patterns for fractions extracted from column 5 in each of the separations. FIG. 2 shows the high and low limits of mass signals observed (approximately 2–5% of maximum signal) in fractions collected from the six columns, and also for the material in eluted fractions (sample 7 onwards), the results for the three successive separations being identified by the codes MP2, MP3 and MP4 respectively. These results show an increasingly improving fraction homogeneity with respect to the original complex material.

EXAMPLE 2
Purification of Oligonucleotide by Sample Displacement Chromatography 1.5 g of an approximately 60% pure crude 20-mer oligonucleotide (TGTGTGTGTGTGTGTGTGTG) was purified on three anion exchange columns (53 mm×10 mm) packed with Q Sepharose FF (Pharmacia) using 50 mM borate buffer, pH 9.8, as carrier. The same separation was performed with and without a pre-column (30 cm×10 mm internal diameter) packed with Source 30 RPC (Pharmacia). During sample application, the components were allowed to distribute over the RPC column according to hydrophobicity, but the actual ion exchange SDC separation was conducted in carrier containing 20% methanol in order to elute the sample from the pre-column onto the separation columns.

HPLC anion exchange analysis (Dionex Nucleopac PA100, gradient of $NaClO_4$ in 10 mM NaOH) revealed a considerably improved purity profile over the columns when the precolumn was inserted in the flow path.

EXAMPLE 3
Peptide Purification Using Gel Permeation Chromatography and Reversed Phase Sample Displacement Chromatography Purification of a 65% pure crude peptide (YADKITEDLK) by sample displacement chromatography alone gives the desired product with significantly higher purity. However, two deletion sequences lacking alanine and threonine respectively are difficult to remove, so that the overall product purity is 92–93%.

In a separation according to the invention, a solution of 200 mg crude peptide in 0.1% acetic acid is applied by gravity flow to a 30 ml (50 cm×9 mm internal diameter) gel permeation chromatography column packed with Sephadex G15 in 0.1% acetic acid. The eluate is continuously collected in tubing that is connected via a valve to the column outlet. After passage of an appropriate volume of eluate the flow is stopped, and the valve is switched so that the eluate is applied in reverse order onto the reversed phase column system described in Example 1. The columns are then disconnected and individually extracted with methanol. HPLC analysis of the resulting fractions is compared with that of fractions obtained from a sample displacement separation alone.

EXAMPLE 4
Purification of Bacitracin 1 g bacitracin (Sigma B-0125) was purified on a 10 ml cation exchange column using 0.1% acetic acid as carrier. After separation, the product was extracted from the column using 0.1 M ammonium acetate, and the extract was collected in fractions. Analysis showed that the purity of bacitracin A increased over a number of fractions, thus creating a purity gradient. Fractions containing bacitracin A as major component were divided in two parts. The first parts were collected in a pool, whereas the second parts were kept separately.

The pooled material was applied to the reversed phase column system described in Example 1, using 0.1% acetic acid as carrier, whereafter the columns were disconnected, individually extracted with methanol and re-equilibrated. They were then reconnected in series and used to separate the non-pooled material, the fractions being applied in order of their elution from the cation exchange column. The columns were again disconnected and individually extracted with methanol.

Figure 3:
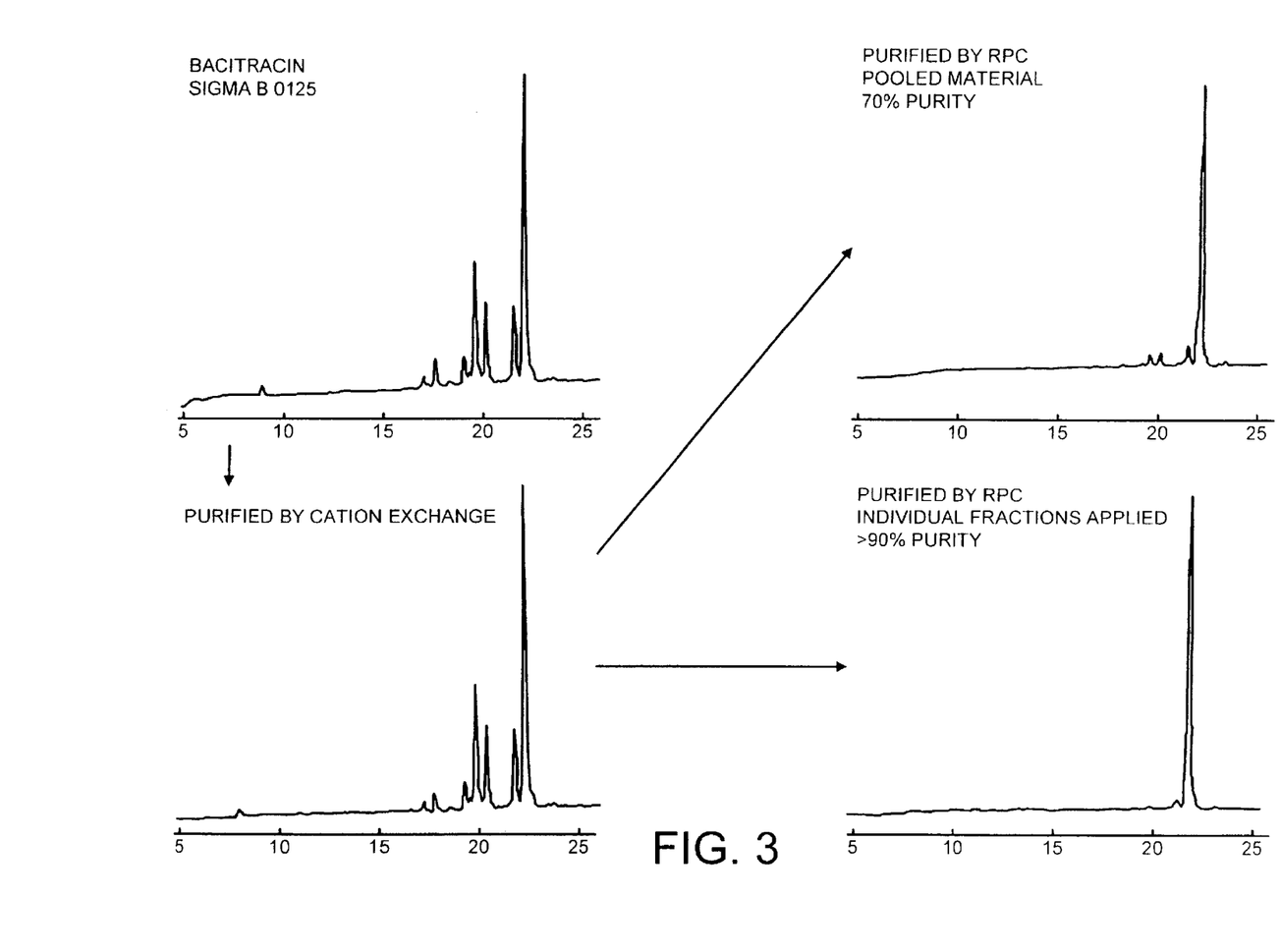
FIG. 3 illustrates the respective Bacitracin purities achieved using the various separation techniques described in Example 4.

Reversed phase HPLC analysis of the extracted material showed that product collected from the second separation contained bacitracin A in much higher purity than did the fractions from the first separation. In both experiments, column number 2 contained the material of highest purity. However, the purity of the product exceeded 90% when the cation exchange fractions were applied sequentially, whereas only 77% purity was obtained following application of the pooled fractions. These results are illustrated in FIG. 3.

What is claimed is:

1. A method of sample displacement chromatography separation which comprises applying a multicomponent sample to one end of a chromatography bed comprising stationary phase material having affinity for components of the sample, causing components of the sample to become distributed along the chromatography bed by passage over the bed of a non-eluting mobile solvent phase, and recovering a desired component of the sample from at least a portion of the chromatography bed, characterised in that sample components are applied to the chromatography bed in a non-homogeneous manner such that the concentration of at least one component with relatively low affinity for the stationary phase material is enhanced during an earlier part of sample application and/or the concentration of at least one component with relatively high affinity for the stationary phase material is enhanced during a later part of sample application.

2. A method as claimed in claim 1 wherein said sample displacement chromatography separation involves reversed phase chromatography.

3. A method as claimed in claim 2 wherein application in a non-homogeneous manner is achieved by loading a solid sample onto said chromatography bed and eluting with a carrier solvent which dissolves the components of said solid sample at differing rates.

4. A method as claimed in claim 2 wherein said multi-component sample is derived from a previous chromatographic separation.

5. A method as claimed in claim 4 wherein said previous chromatographic separation involves use of a divisible sample displacement chromatography column.

6. A method as claimed in claim 5 wherein said divisible sample displacement chromatography column is a reversed phase chromatography column, ion exchange column, or hydrophobic interaction column.

7. A method as claimed in claim 4 wherein said previous chromatographic separation involves gel permeation chromatography, ion exchange chromatography or reversed phase chromatography.

8. A method as claimed in claim 1 wherein said multi-component sample is derived from a previous chromatographic separation.

9. A method as claimed in claim 8 wherein said previous chromatographic separation involves use of a divisible sample displacement chromatography column.

10. A method as claimed in claim 9 wherein said divisible sample displacement chromatography column is a reversed phase chromatography column, ion exchange column, or hydrophobic interaction column.

11. A method as claimed in claim 8 wherein said previous chromatographic separation involves gel permeation chromatography, ion exchange chromatography or reversed phase chromatography.

12. A method as claimed in claim 1 wherein application in a non-homogeneous manner is achieved by loading a solid sample onto said chromatography bed and eluting with a carrier solvent which dissolves the components of said solid sample at differing rates.

* * * * *